(12) United States Patent
Ollmann et al.

(10) Patent No.: US 11,426,328 B1
(45) Date of Patent: Aug. 30, 2022

(54) CLOSURE FOR A MEDICAL CONTAINER

(71) Applicants: Alexander Ollmann, Delray Beach, FL (US); Robert Banik, Hollywood, FL (US); Peter Lehel, Boca Raton, FL (US)

(72) Inventors: Alexander Ollmann, Delray Beach, FL (US); Robert Banik, Hollywood, FL (US); Peter Lehel, Boca Raton, FL (US)

( * ) Notice: Subject to any disclaimer, the term of this patent is extended or adjusted under 35 U.S.C. 154(b) by 341 days.

(21) Appl. No.: 16/558,991

(22) Filed: Sep. 3, 2019

Related U.S. Application Data

(60) Provisional application No. 62/725,706, filed on Aug. 31, 2018.

(51) Int. Cl.
*A61J 1/14* (2006.01)
*A61M 5/31* (2006.01)

(52) U.S. Cl.
CPC .............. *A61J 1/1412* (2013.01); *A61M 5/31* (2013.01); *A61M 2005/3104* (2013.01); *A61M 2205/586* (2013.01)

(58) Field of Classification Search
CPC ......... A61J 1/1412; B65D 51/00; A61M 5/31; A61M 2005/3104; A61M 2205/586
USPC ................................................. 220/200, 287
See application file for complete search history.

(56) References Cited

U.S. PATENT DOCUMENTS

| | | | |
|---|---|---|---|
| 722,943 A | 3/1903 | Chappell | |
| 732,662 A | 6/1903 | Smith | |
| 1,678,991 A | 7/1928 | Marschalek | |
| 1,970,631 A | 8/1934 | Sherman | |
| 2,477,598 A | 8/1949 | Hain | |
| 2,739,590 A | 3/1956 | Yochem | |
| 2,823,674 A | 2/1958 | Yochem | |
| 2,834,346 A | 5/1958 | Adams | |
| 2,875,761 A | 3/1959 | Helmer et al. | |
| 2,888,015 A | 5/1959 | Hunt | |
| 2,952,255 A | 9/1960 | Hein, Jr. | |
| 3,122,280 A | 2/1964 | Goda | |
| 3,245,567 A | 4/1966 | Knight | |

(Continued)

FOREIGN PATENT DOCUMENTS

| EP | 0148116 A | 7/1985 |
|---|---|---|
| GB | 486367 | 6/1938 |

(Continued)

OTHER PUBLICATIONS

Arai Tsugio, Pilfering Proof Cap, Jan. 1, 1996.

*Primary Examiner* — Timothy L Maust
(74) *Attorney, Agent, or Firm* — Malloy & Malloy, PL; Jennie S. Malloy; Peter A. Matos

(57) ABSTRACT

A closure for a medical container including a base structured to be supported in an operative, upright orientation on a horizontal surface and having an exposed face and a connector disposed thereon and extending outwardly therefrom. A protective cage includes one or more cage members each configured in the form of a helix fixedly connected to the base and extending longitudinally and laterally outward from the connector in at least partially surrounding relation thereto. The base may include self-righting structural features, including an outer surface having a curved, substantially bulbous configuration and a center of gravity disposed between a tipping point of said base and a terminal end thereof.

18 Claims, 4 Drawing Sheets

(56) References Cited

U.S. PATENT DOCUMENTS

| | | | |
|---|---|---|---|
| 3,323,798 A | 6/1967 | Miller | |
| 3,364,890 A | 1/1968 | Andersen | |
| 3,368,673 A | 2/1968 | Johnson | |
| 3,574,306 A | 4/1971 | Alden | |
| 3,598,120 A | 8/1971 | Mass | |
| 3,610,241 A | 10/1971 | LeMarie | |
| 3,700,215 A | 10/1972 | Hardman et al. | |
| 3,706,307 A | 12/1972 | Hasson | |
| 3,712,749 A | 1/1973 | Roberts | |
| 3,726,445 A | 4/1973 | Ostrowsky et al. | |
| 3,747,751 A | 7/1973 | Miller et al. | |
| 3,872,867 A | 3/1975 | Killinger | |
| 3,904,033 A | 9/1975 | Haerr | |
| 3,905,375 A | 9/1975 | Toyama | |
| 3,937,211 A * | 2/1976 | Merten | A61B 5/150908 |
| | | | 600/578 |
| 3,987,930 A | 10/1976 | Fuson | |
| 4,043,334 A * | 8/1977 | Brown | A61M 5/3134 |
| | | | 604/199 |
| 4,046,145 A | 9/1977 | Choksi et al. | |
| 4,068,696 A | 1/1978 | Winchell | |
| 4,216,585 A | 8/1980 | Hatter | |
| 4,216,872 A | 8/1980 | Bean | |
| 4,244,366 A | 1/1981 | Raines | |
| 4,252,122 A | 2/1981 | Halvorsen | |
| 4,271,972 A | 6/1981 | Thor | |
| 4,286,591 A | 9/1981 | Raines | |
| 4,286,640 A | 9/1981 | Knox et al. | |
| 4,313,539 A | 2/1982 | Raines | |
| 4,369,781 A | 1/1983 | Gilson et al. | |
| 4,420,085 A | 12/1983 | Wilson et al. | |
| 4,430,077 A | 2/1984 | Mittleman et al. | |
| 4,457,445 A | 7/1984 | Hanks et al. | |
| 4,482,071 A | 11/1984 | Ishiwatari | |
| D277,783 S | 2/1985 | Beck | |
| 4,521,237 A | 6/1985 | Logothetis | |
| 4,530,697 A | 7/1985 | Kuhlemann et al. | |
| 4,571,242 A | 2/1986 | Klein et al. | |
| 4,589,171 A | 5/1986 | McGill | |
| 4,664,259 A | 5/1987 | Landis | |
| 4,667,837 A | 5/1987 | Vitello et al. | |
| 4,676,530 A | 6/1987 | Nordgren et al. | |
| 4,693,707 A | 9/1987 | Dye | |
| 4,726,483 A | 2/1988 | Drozd | |
| 4,742,910 A | 5/1988 | Staebler | |
| 4,743,229 A | 5/1988 | Chu | |
| 4,743,231 A | 5/1988 | Kay et al. | |
| 4,760,847 A | 8/1988 | Vaillancourt | |
| 4,813,564 A | 3/1989 | Cooper et al. | |
| 4,832,695 A | 5/1989 | Rosenberg et al. | |
| 4,834,706 A | 5/1989 | Beck et al. | |
| 4,842,592 A | 6/1989 | Caggiani et al. | |
| 4,844,906 A | 7/1989 | Hermelin et al. | |
| 4,906,231 A | 3/1990 | Young | |
| 4,919,285 A | 4/1990 | Roof et al. | |
| 4,936,445 A | 6/1990 | Grabenkort | |
| 5,009,323 A | 4/1991 | Montgomery et al. | |
| 5,024,323 A | 6/1991 | Bolton | |
| 5,049,129 A | 9/1991 | Zdeb et al. | |
| 5,057,093 A | 10/1991 | Clegg et al. | |
| D323,392 S | 1/1992 | Byrne | |
| 5,085,332 A * | 2/1992 | Gettig | B65D 51/18 |
| | | | 215/249 |
| 5,090,564 A | 2/1992 | Chimienti | |
| 5,135,496 A | 8/1992 | Vetter et al. | |
| 5,163,922 A * | 11/1992 | McElveen, Jr. | A61M 39/02 |
| | | | 251/149.1 |
| 5,165,560 A | 11/1992 | Enniss, III et al. | |
| 5,230,429 A | 7/1993 | Etheredge, III | |
| 5,267,983 A | 12/1993 | Oilschlager et al. | |
| 5,292,308 A | 3/1994 | Ryan | |
| 5,293,993 A | 3/1994 | Yates, Jr. et al. | |
| 5,295,599 A | 3/1994 | Smith | |
| 5,312,367 A | 5/1994 | Nathan | |
| 5,312,368 A | 5/1994 | Haynes | |
| 5,328,466 A | 7/1994 | Denmark | |
| 5,328,474 A | 7/1994 | Raines | |
| 5,356,380 A | 10/1994 | Hoekwater et al. | |
| 5,370,226 A | 12/1994 | Gollobin et al. | |
| 5,380,295 A | 1/1995 | Vacca | |
| 5,402,887 A | 4/1995 | Shillington | |
| 5,405,339 A | 4/1995 | Kohnen et al. | |
| 5,456,668 A | 10/1995 | Ogle, II | |
| 5,458,580 A | 10/1995 | Hajishoreh | |
| 5,468,224 A | 11/1995 | Souryal | |
| 5,531,695 A | 7/1996 | Swisher | |
| 5,540,666 A | 7/1996 | Barta et al. | |
| 5,549,571 A | 8/1996 | Sak | |
| 5,558,648 A | 9/1996 | Shields | |
| 5,584,817 A | 12/1996 | van den Haak | |
| 5,588,239 A | 12/1996 | Anderson | |
| 5,624,402 A | 4/1997 | Imbert | |
| 5,662,233 A | 9/1997 | Reid | |
| 5,674,209 A | 10/1997 | Yarger | |
| 5,695,470 A | 12/1997 | Roussigne et al. | |
| 5,700,247 A | 12/1997 | Grimard et al. | |
| 5,702,374 A | 12/1997 | Johnson | |
| 5,713,485 A | 2/1998 | Lift et al. | |
| 5,776,124 A | 7/1998 | Wald | |
| 5,785,691 A | 7/1998 | Vetter et al. | |
| 5,797,885 A | 8/1998 | Rubin | |
| 5,807,343 A | 9/1998 | Tucker et al. | |
| D402,766 S | 12/1998 | Smith et al. | |
| 5,883,806 A | 3/1999 | Meador et al. | |
| 5,884,457 A | 3/1999 | Ortiz et al. | |
| 5,902,269 A | 5/1999 | Jentzen | |
| 5,951,522 A | 9/1999 | Rosato et al. | |
| 5,951,525 A | 9/1999 | Thorne et al. | |
| 5,954,657 A | 9/1999 | Rados | |
| 5,957,166 A | 9/1999 | Safabash | |
| 5,957,314 A | 9/1999 | Nishida et al. | |
| 5,963,136 A | 10/1999 | O'Brien | |
| 5,989,227 A | 11/1999 | Vetter et al. | |
| 5,993,437 A | 11/1999 | Raoz | |
| 6,000,548 A | 12/1999 | Tsals | |
| D419,671 S | 1/2000 | Jansen | |
| 6,021,824 A | 2/2000 | Larsen et al. | |
| 6,027,482 A | 2/2000 | Imbert | |
| 6,068,614 A | 5/2000 | Kimber et al. | |
| D430,293 S | 8/2000 | Jansen | |
| D431,864 S | 10/2000 | Jansen | |
| 6,126,640 A | 10/2000 | Tucker et al. | |
| 6,190,364 B1 | 2/2001 | Imbert | |
| 6,193,688 B1 | 2/2001 | Balestracci et al. | |
| 6,196,593 B1 | 3/2001 | Petrick et al. | |
| 6,196,998 B1 | 3/2001 | Jansen et al. | |
| 6,279,746 B1 | 4/2001 | Hussaini et al. | |
| 6,235,376 B1 | 5/2001 | Miyazaki et al. | |
| 6,280,418 B1 | 8/2001 | Reinhard et al. | |
| 6,287,671 B1 | 9/2001 | Bright et al. | |
| 6,322,543 B1 | 11/2001 | Singh et al. | |
| 6,338,200 B1 | 1/2002 | Baxa et al. | |
| 6,358,241 B1 | 3/2002 | Shapeton et al. | |
| 6,375,640 B1 | 4/2002 | Teraoka | |
| 6,394,983 B1 | 5/2002 | Mayoral et al. | |
| 6,439,276 B1 | 8/2002 | Wood et al. | |
| 6,485,460 B2 | 11/2002 | Eakins et al. | |
| 6,500,155 B2 | 12/2002 | Sasso | |
| 6,520,935 B1 | 2/2003 | Jansen et al. | |
| 6,540,697 B2 | 4/2003 | Chen | |
| 6,565,529 B1 | 5/2003 | Kimber et al. | |
| 6,581,792 B1 | 6/2003 | Limanjaya | |
| 6,585,691 B1 | 7/2003 | Vitello | |
| 6,592,251 B2 | 7/2003 | Edwards et al. | |
| 6,666,852 B2 | 12/2003 | Niedospial, Jr. | |
| 6,682,798 B1 | 1/2004 | Kiraly | |
| 6,726,652 B2 | 4/2004 | Eakins et al. | |
| 6,726,672 B1 | 4/2004 | Hanley et al. | |
| 6,755,220 B2 | 6/2004 | Castellano et al. | |
| 6,764,469 B2 | 7/2004 | Broselow | |
| 6,796,586 B2 | 9/2004 | Werth | |
| 6,821,268 B2 | 11/2004 | Balestracci | |
| D501,549 S | 2/2005 | McAllister et al. | |
| 6,921,383 B2 | 7/2005 | Vitello | |

(56) References Cited

U.S. PATENT DOCUMENTS

| | | |
|---|---|---|
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 * | 9/2013 | Bisio ................ B65D 41/3433 |
| | | 215/252 |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 * | 4/2015 | Tamarindo ............ B65D 51/24 |
| | | 206/508 |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,758,684 B1 | 9/2020 | Vitello et al. |
| 10,773,067 B2 * | 9/2020 | Davis .................... A61M 39/10 |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |

(56) References Cited

U.S. PATENT DOCUMENTS

| | | |
|---|---|---|
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0182686 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2019/0388626 A1 | 12/2019 | Okihara |

FOREIGN PATENT DOCUMENTS

| | | |
|---|---|---|
| JP | 08002544 | 1/1996 |
| WO | WO 2008/000279 | 1/2008 |
| WO | WO 2017086607 | 5/2015 |

\* cited by examiner

CLOSURE FOR A MEDICAL CONTAINER

CLAIM OF PRIORITY

The present Non-Provisional patent application claims priority pursuant to 35 U.S.C. Section 119(e) to a prior filed Provisional patent application, namely, that having Ser. No. 62/725,706 filed on Aug. 31, 2018, the contents of which is incorporated herein by reference in its entirety.

BACKGROUND OF THE INVENTION

Field of the Invention

A closure for a medical container such as, but not limited to, a syringe, wherein the closure includes a base having a connector mounted thereon and a protective cage disposed in surrounding relation to the connector. The base may have self-righting capabilities and the connector may vary in configuration to facilitate attachment to a compatible connector, associated with the medical container/syringe.

Description of the Related Art

In the manufacturing process, mass production of different types of medical devices frequently requires careful alignment of the different components thereof, in order to establish a proper assembly. With small components such as closures, tip caps, etc. it is sometimes best to randomly disperse the various components on a working surface and manually orient and align compatible components which are to be connected to one another.

However, in an environment where sterility is to be maintained, it is not feasible to manually handle the various components such as, but not limited to, a slip taper connector and still avoid contamination of the interconnected portions. Manual contact or engagement of the type described can cause contamination of the entire system. Therefore, the ability to structure a base or other portion of a medical component in a manner to include self-righting capabilities would save valuable time in the assembly procedure. As well as possibly facilitate maintaining the sterility of such components.

Accordingly, there is a need in the industry associated with the manufacture, assembly and use of medical components including, but not limited to closures, caps, etc., which overcomes the assembly problems of the type set forth above while facilitating the maintenance of sterility. More specifically, there is a need for a closure, cover, cap, or like structure for a medical container such as, but not limited to, various types of syringes which includes a predetermined connector.

Moreover, the connector associated with an improved and proposed closure may vary in structure and configuration in order to be compatible with the connector associated with the medical container or syringe, to which it is to be connected. By way of nonlimiting example, the connector associated with an improved closure may be structured as, but not limited to, an oral or enteral connector; Lure slip female connector; Lure slip male connector; Luer lock female connector; Luer lock male connector; neuraxial female connector and/or neuraxial male connector.

In addition, the sterility of the medical closure and/or its parts may be facilitated by the inclusion of a protective cage disposed in at least partially surrounding relation to the connector. As a result, a preferred and proposed closure would include any of a plurality of predetermined connectors disposed in surrounded, protected relation by a protective cage. Further, in order to assure a proper and accurate alignment and interconnection, the protective cage should be dimensioned, structured and configured to facilitate a connecting engagement of a connector on the medical container, which is compatible with the connector on the closure. In contrast, structural and operative features of the protective cage could also facilitate prevention of mis-connections between incompatible connectors disposed on the medical container/syringe and on the closure.

SUMMARY OF THE INVENTION

The present invention is directed to a closure for a medical container such as, but not limited to, any one of a plurality of syringes structured to administer content thereof in different ways. Further, the closure includes a connector mounted on and extending outwardly from a supportive base. As a result, the closure may be in the form of a tip cap, or other type of closure, having a connector which is specifically structured and/or configured to be compatible with the connector associated with the syringe or other type of medical container. Further, when the closure is in the form of a tip cap interconnection of the closure with the connector of the syringe/medical container will establish a fluid sealing connection therewith.

Therefore, the structure and configuration of the connector associated with the closure may vary to accommodate a fluid sealing attachment with a correspondingly compatible connector mounted on the syringe. By way of nonlimiting example, different ones of a plurality of closures of the present invention may each include a different connector such as, but not limited to, an oral or enteral connector; Lure slip female connector; Lure slip male connector; Luer lock female connector; Luer lock male connector; neuraxial female connector and/or neuraxial male connector.

In addition, the base includes an exposed face defined by an outer exposed surface area. The preferred or predetermined connector is fixedly or integrally disposed on the exposed face and extends axially outward therefrom a sufficient distance to facilitate the aforementioned attachment or connection to the compatible connector associated with the syringe/medical container.

As set forth herein, one problem associated with the assembly of closures and/or the different components associated therewith is the maintenance of sterility thereof, which is especially important in a medical environment. Accordingly, the closure of the present invention includes a protective cage fixedly or integrally connected to the base and extending outwardly therefrom in protective, at least partially surrounding relation to the connector. Further, the cage comprises at least one or alternatively a plurality of cage members. As such, the one or more cage members are dimensioned, disposed and configured to define the aforementioned protective, surrounding disposition of the cage, relative to the connector.

More specifically, in one or more preferred embodiments of the closure of the present invention, each of the one or more cage members is configured in the form of a helix. As such each of the helices includes one end fixedly or integrally connected to the exposed face in laterally outward relation to the connector. The one or more helices also include a sufficient length to extend longitudinally or axially outward from the exposed face in the surrounding relation to the connector. As a result, the outer or free ends of each of the helical cage members are disposed at least somewhat above the free end of the connector.

Further, the dimension, configuration and disposition of the one or more helices require that the connector of the syringe/medical container pass through an open end of the cage, on an interior of the one or more helices and into the intended attachment with the connector mounted on with the base. Therefore, the cage may be accurately defined as including an open outer end, which facilitates "connector access" to the connector. The syringe/medical container and its connector bus pass through the open end of the cage to establish the fluid sealing or other predetermined attachment with the connector associated with the base of the closure. As explained in greater detail herein, aforementioned open end of the cage or connector access may also be disposed dimensioned and configured to at least partially restrict access of the medical container and the connector associated there with.

In more specific terms, the free ends of the one or more helices and/or portions of the respective lengths thereof, may be disposed in interruptive engagement with the medical container and/or its connector upon an attempted attachment of the medical container to the closure. By virtue of such interruptive positioning, the medical container and its connector may be prevented or at least initially restricted from attachment with the connector of the closure. Such preventive or restrictive engagement of the one or more helices with the medical container may be at least partially dependent on the degree of rigidity of the one or more helices defining the cage members of the cage.

Therefore, each of the one or more helices may be formed of a substantially rigid, non-collapsible material. As a result, interruptive engagement of the one or more helices with the medical container and/or its connector may result in the prevention of incompatible connectors of the medical container and closure. Such interruptive engagement may be at least partially based on the dimension and/or configuration of the medical container which includes a connector, which is incompatible with the connector associated with the closure. In turn dangerous or potentially fatal mis-connections between incompatible connectors may be prevented.

In contrast one or more additional embodiments of the closure of the present invention may include the one or more helices associated there with being formed of a flexible at least partially collapsible material. In this contrasting embodiment, attempts to attach a medical container and its compatible connector will result in an at least partial collapse or inward folding of the one or more helices, defining the one or more cage members, as the connector of the medical container passes through the open end of the cage into attached engagement with the compatible connector of the closure.

Additional structural features of the different embodiments of the closure of the present invention include the structuring of the base to have self-righting capabilities. More specifically, one or more embodiments of the base may include an outer surface having a curved, substantially bulbous configuration extending from a "tipping-point" to a terminal end segment located on a distal portion of the base, opposite to the exposed face.

As explained in greater detail hereinafter, the dimension, structure and configuration of the closure and in particular the base defines the "tipping-point" as a portion of the base coincident with the outer peripheral edge of the exposed face. Such a location or portion of the base is defined as the "tipping-point" due to the fact that orientation of the closure beyond the outer periphery of the exposed face would normally result in contact of the connector with a supporting surface.

The self-righting structure and characteristics of the base is further defined by a location of the center of gravity of the base between the tipping point and the terminal end segment of the base. Such location of the center of gravity will have the inherent tendency, in cooperation with the curved, bulbous outer surface of the base, to dispose the closure in a vertical or operatively upright orientation when disposed on a horizontal supporting surface.

As should be apparent such an upright orientation facilitates an aligned mating attachment or engagement with the connector of the medical container and result in a significant savings of time associated with the assembly and/or connection of the closure with the medical container. The upright orientation is further facilitated by the aforementioned end segment of the base having a flat configuration in order to provide stability to the upright orientation of the closure, when so disposed on the horizontal supporting surface.

Therefore, the structural and operative features of the various embodiments of the closure of the present invention overcome the well-recognized disadvantages and problems associated with the manufacture, assembly and use of medical components of the type set forth herein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
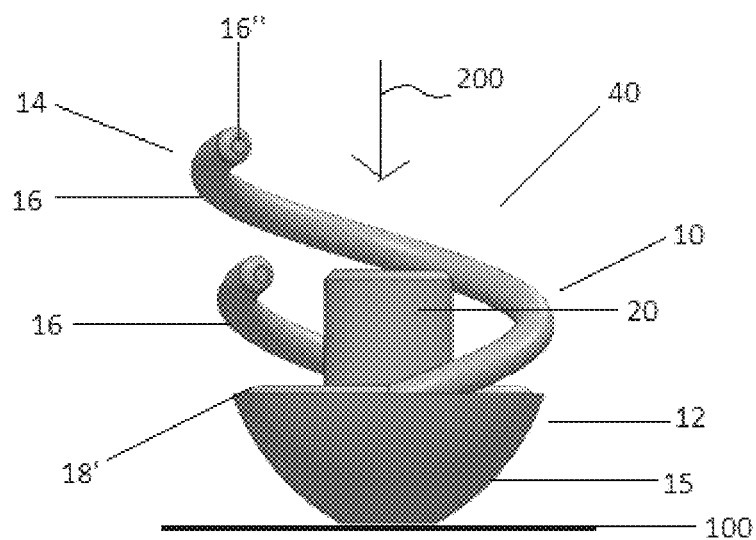
FIG. 1 is a front elevation of one embodiment of the closure of the present invention.

As represented in the accompanying Figures, the present invention is directed to a closure generally indicated as 10 including a base 12. The base 12 may include one of a plurality of different, predetermined connectors 20-26 as represented throughout FIGS. 1-8. In addition, each of a plurality of closures 10 includes a protective cage, generally indicated as 14. Each cage 14 includes at least one or alternatively a plurality of cage members 16. Further, each of the plurality of cage members 16 as well as a preselected one of the connectors 20-26 are fixedly or integrally connected to an outer, exposed face 18 of the base 12 and extend axially or longitudinally outward from the exposed face 18.

As clearly indicated by a comparison of the embodiments of FIGS. 1-8 the number of cage member 16 may vary. In more specific terms, the embodiments of FIGS. 3-7 include a single cage member 16 in the form of a helix. In contrast, the embodiment of FIGS. 1-2 includes a plurality of two cage members 16, each configured to define a helix. In further contrast, the embodiment of FIG. 8 comprises a plurality of three cage members 16 each having a helical configuration. Also, all of the cage members of a single closure 10 may be defined as "left-handed" helices (see FIGS. 1 and 2) or right-handed helices (See FIGS. 3-8). Further, as commonly defined a "right-handed" helix moves around its axis and a clockwise direction from beginning to end. In contrast a "left-handed" helix moves around its axis in a counterclockwise direction from beginning to end.

Figure 2:
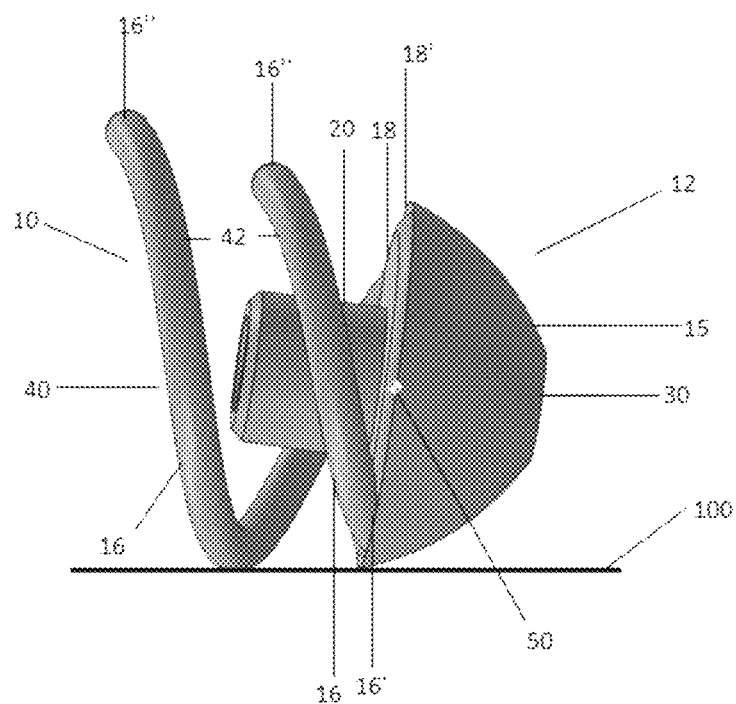
FIG. 2 is a side view of the embodiment of FIG. 1 in an at least partially "tipped" orientation.

A comparison of the embodiments of the closure 10 as represented in FIGS. 1 and 2 with the embodiments of the closure 10 as represented in FIGS. 3-8 further indicate that the cross sectional configuration of the one or more helical cage members 16 may vary. By way of non-limiting example, the cross-section of each of the cage member 16 may have a substantially round or circular configuration. In contrast, the cross-section of each of the helical cage members 16 may be half-rounded or partially flattened on an interior surface thereof. It is also noted that the cross sectional configuration of each of the helical cage members 16 of the embodiments of FIGS. 3-8 may have advantages which facilitate the manufacturing thereof using injection molding.

The base further includes a terminal end segment 30 disposed at a distal end of the base 12, opposite to the exposed face 18. The terminal end segment 30 has a flat configuration which facilitates the stable disposition of each of the closures 10 in an operative, upright orientation, on a horizontal support surface 100, as represented in at least FIG. 1. As explained in greater detail hereinafter, the base 12 has self-righting capabilities allowing it to normally and "automatically" assume the operative, upright position of FIG. 1, without manual alignment, such as when randomly dispersed on the horizontal support surface 100.

As set forth herein, one problem associated with assembling closures and/or the different components associated therewith, is the maintenance of sterility, which is especially important in a medical environment. Accordingly, each of the closures 10 of the present invention includes the protective cage 14 fixedly or integrally connected to the base 12 and extending outwardly therefrom in protective, at least partially surrounding relation to a corresponding one of the connectors 20-26. Further, the one or more cage members 16 are dimensioned, disposed and configured to define the aforementioned protective, surrounding disposition of the cage, relative to a corresponding one of the connectors 20-26.

More specifically, in the represented embodiments of FIGS. 1-8, each closure 10 includes its cage 14 having the one or more cage members 16 each being configured in the form of a helix. For purposes of clarity, the reference numeral "16" will be used to indicate the one or more cage members, as well as the helical configuration thereof. Therefore, the terms cage member, helix and/or helices will be used synonymously.

Figure 8:
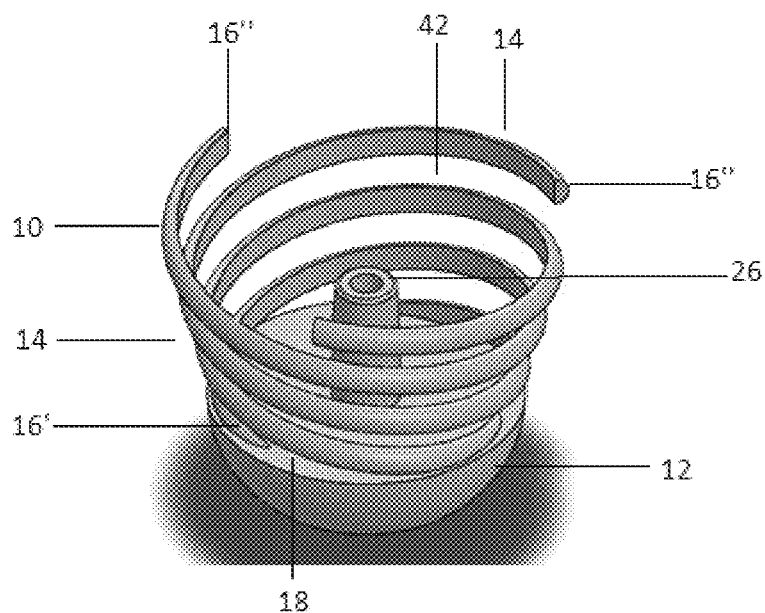
FIG. 8 is a top perspective view of yet another embodiment of the closure of the present invention.

Each of the helices 16 includes one end 16' fixedly or integrally connected to the exposed face 18 in laterally outward relation to the corresponding connector 20-26. As further represented, each of the fixed ends 16' is located adjacent to and/or coincident with the outer peripheral edge 18' of the exposed face 18. As a result, each of the helices or cage members 16 are disposed laterally outwardly a sufficient spaced distance to allow access to the connector 20-26 by another, compatible connector, attached to the medical container/syringe (not shown for purposes of clarity). As also represented throughout the Figures, the helices or cage members 16 also includes a sufficient length to extend longitudinally or axially (coaxial to the corresponding connector 20-26) outward from the exposed face 18 in the surrounding relation to the connector 20-26. As a result, the outer or free end 16" of each of the helices or cage members 16 are disposed above the corresponding connector 20-26. The term "above" refers to a location of the free ends 16" when the closure 10 is in the upright orientation of FIG. 1. Further, when a plurality of helical cage members 16 are connected to the same closure 10, each may extend longitudinally or axially outward from the exposed face 18 to a location somewhat above or outwardly from the free end of the corresponding connector 20-26, as represented in FIGS. 1, 2 and 8.

As a result, the dimension, configuration and disposition of the one or more helices or cage members 16 require that a connector of the syringe/medical container (not shown for purposes of clarity) pass through an open end, generally indicated as 40, of the cage 14. The passage of the medical container/syringe and its associated connector is schematically represented by directional arrow 200 in FIG. 1. Therefore as represented, the medical container and its connector 200 passes through the open end 40 and through, and on the interior of, the one or more helices or cage members 16, into an intended attachment with the connector 20-26 associated with the respective bases 12.

Moreover, the cage 14 may be accurately described as including an open outer end 40 which at least partially defines a connector access path. In order to establish a fluid tight connection with a corresponding one of the compatible connectors 20-26 of the closure 10, the medical container and its connector must pass through the open end 40 and at least through an interior portion of cage 14, inside the one or more helices or cage members 16.

The open end or connector access 40 of each cage 14 may also be disposed, dimensioned and configured to at least partially restrict access of the medical container and the connector associated there with. In more specific terms, the free ends 16" of the one or more helices 16 and or portions of the respective lengths thereof may be disposed in interruptive engagement with the medical container and/or its connector, upon an attempted attachment of the medical container to the closure 10. By virtue of such interruptive positioning, the medical container and its connector may be prevented or at least initially restricted from attachment with the connector 20-26 of the closure 10. Such preventive or restrictive engagement of the one or more helices 16 with the medical container may be at least partially dependent on the degree of rigidity of the one or more helical cage members 16 defining the cage 14.

Therefore, each of the one or more helices or cage members 16 may be formed of a substantially rigid, non-collapsible material. As a result, interruptive engagement of the one or more helices 16 with the medical container and/or its connector may result in preventing the medical container and its connector from reaching the connector 20-26 of the corresponding closure 10. Such a preventive attachment will eliminate mis-connections of incompatible connectors of the medical container and closure 10. In turn dangerous or potentially fatal mis-connections between incompatible connectors may be prevented. It is noted herein that because each of the cage member 16 have the aforementioned helical configuration, they may in fact be at least minimally collapsed even if they are formed from a rigid material. However, the degree of rigidity of each of the helical cage member 16 will be such as to allow only a minimal or considerably small amount of collapse. Further, as used herein the term "collapse" is meant to describe a closure of the spacing 42 between a plurality of helical cage members 16 associated with a single closure 10 or a forced movement of one or more of the helical cage members 16 towards the exposed face 18.

In contrast, one or more additional embodiments of the one or more closures 10 of the present invention may include the one or more helices 16 associated there with being formed of a flexible, at least partially collapsible material. In this contrasting embodiment, attempts to attach a medical container and its compatible connector will result in an at least partial collapse or inward folding of the one or more helices 16. Such a collapse of the plurality of helices or cage members 16 of a common closure 10 will be evidenced by a closure of the spacing 42 between the different helices or cage member 16. Such at least partial collapse or folding will occur as the connector of the medical container passes through the open end 40 of the cage 14, into attached engagement with the compatible connector 20-26 of the corresponding closure 10.

As indicated above, the additional structural features of the different embodiments of the closure 10 may include the structuring of the base 12 to have self-righting capabilities. As such, the self-writing structure of the base 12 may include an outer surface 15 having a curved, substantially bulbous configuration extending from a "tipping-point" 50 to the flat terminal end segment 30, located on a distal portion of the base 12, opposite to the exposed face 18.

As represented in FIG. 2, the "tipping-point" 50 may be disposed and/or defined as a portion of the base 12 coincident with the outer peripheral edge 18' of the exposed face 18. Such a location or portion of the base 12 is defined as the "tipping-point" 50 due to the fact that orientation of the closure 10 and/or base 12 beyond the outer periphery 18' of the exposed face 18, would typically result in contact of the connector 20-26 with a supporting surface 100. However, in the preferred embodiments of the present invention, each closure 10 includes the protective cage 14, disposed in surrounding relation to a corresponding connector 20-26. In in the tipped orientation of FIG. 2, the protective cage 14 will prevent actual engagement of the connector 20-26 with the supporting surface 100, in the unlikely event that the cover 10 is disposed in the represented "tipped" orientation.

The self-righting structure and characteristics of the base 12 is further defined by a center of gravity of the base 12 being disposed between the tipping point 50 and the terminal end segment 30 of the base 12 and preferably closer to the terminal end segment 30. Such location of the center of gravity will have the inherent tendency, in cooperation with the curved, bulbous outer surface 15 of the base 12, to dispose the closure 10 in the vertical operatively upright orientation of FIG. 1 when randomly dispersed on a horizontal supporting surface 100.

As should be apparent such an upright orientation facilitates an aligned mating attachment or engagement with the connector of the medical container and results in a significant savings of time associated with the assembling and/or connection of the closure with the medical container. As indicated, the preferred, stable upright orientation is further facilitated by the aforementioned terminal end segment 30 of the base 12 being located coincident to the distal end of the base 12, opposite to the exposed face 18 and having a flat configuration, as indicated.

As also emphasized herein, the structure and configuration of the different connectors 20-26 associated with the different embodiments of the closure 10 may be different to accommodate a fluid sealing or other intended attachment with a correspondingly compatible connector mounted on the syringe/medical container. By way of nonlimiting example, different ones of a plurality of closures 10 of the present invention may each include a different connector such as, but not limited to, an oral or enteral connector; Lure slip female connector; Lure slip male connector; Luer lock female connector; Luer lock male connector; neuraxial female connector and/or neuraxial male connector.

Figure 3:
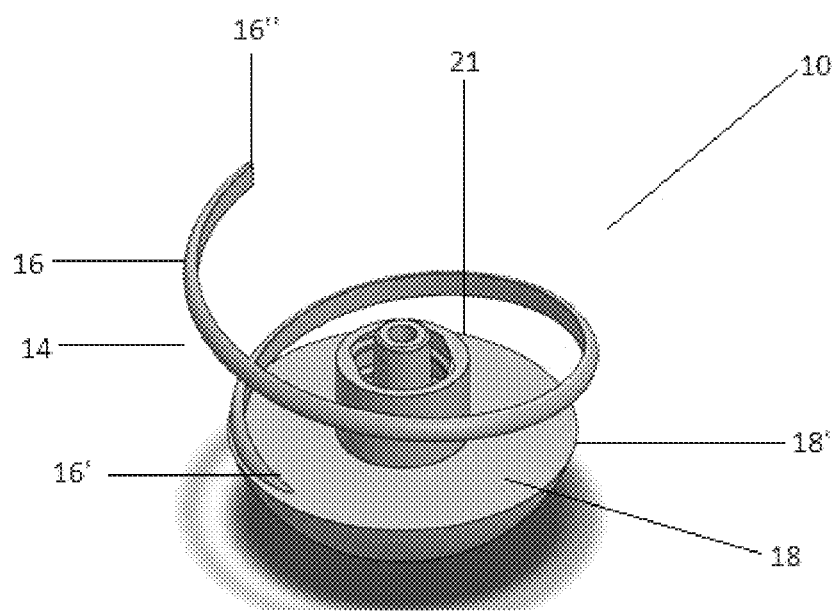
FIG. 3 is a top perspective view of yet another embodiment of the closure of the present invention.
Figure 4:
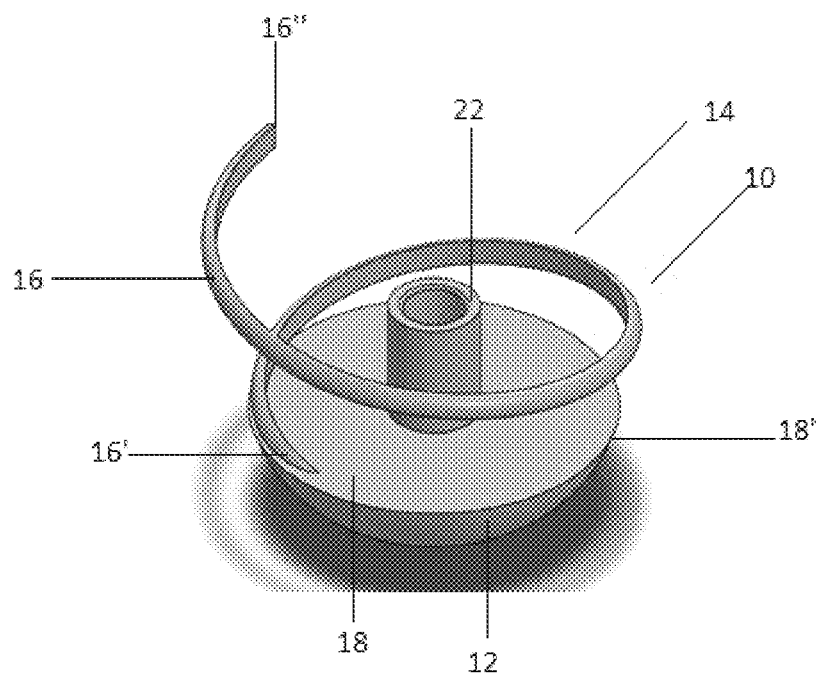
FIG. 4 is a top perspective view of yet another embodiment of the closure of the present invention.
Figure 5:
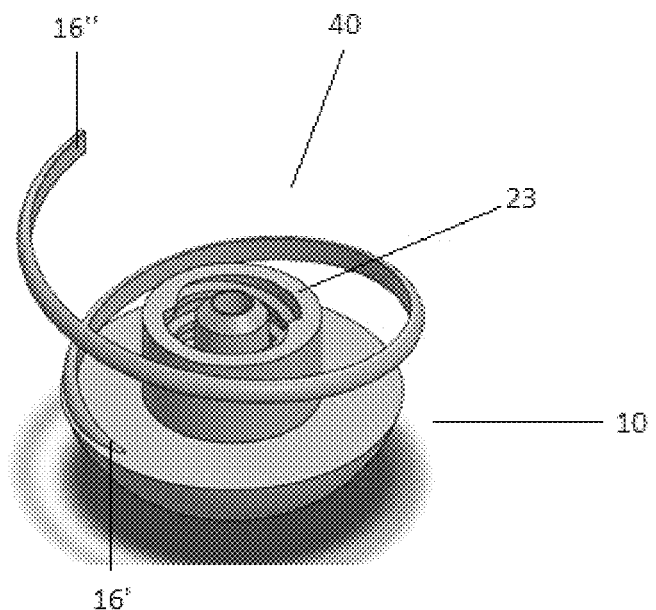
FIG. 5 is a top perspective view of yet another embodiment of the closure of the present invention.
Figure 6:
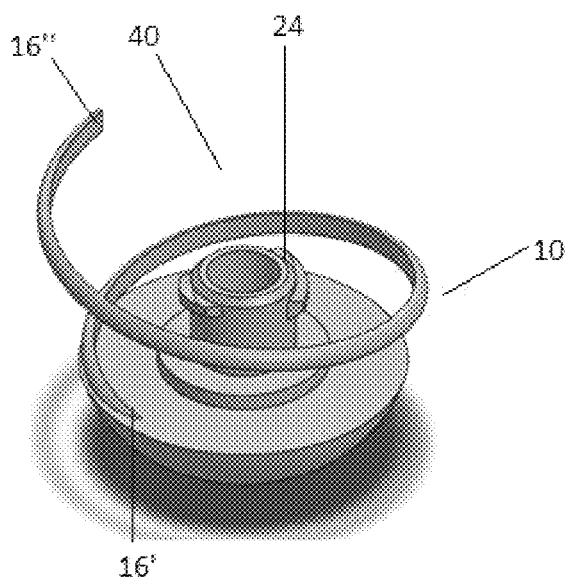
FIG. 6 is a top perspective view of yet another embodiment of the closure of the present invention.
Figure 7:
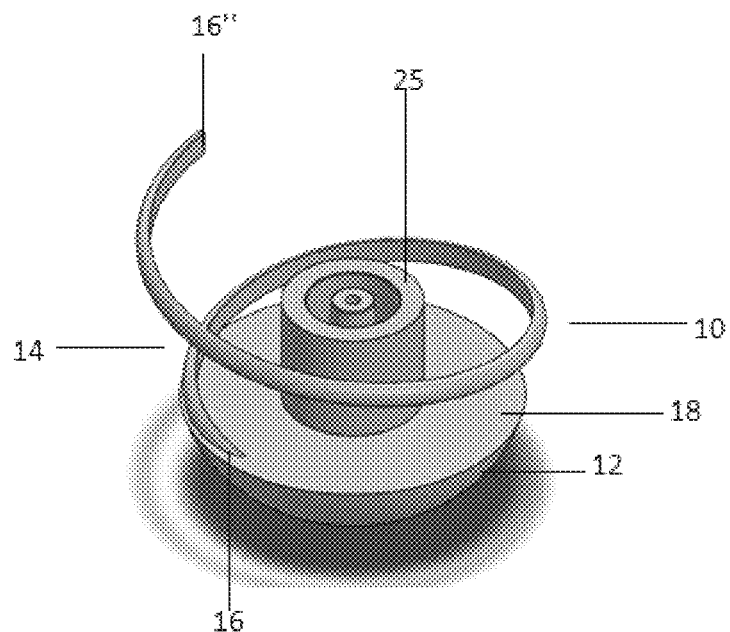
FIG. 7 is a top perspective view of yet another embodiment of the closure of the present invention.

Further by way of example, the embodiment of FIGS. 1, 2 and 4 disclose connectors 20 and 22 representative of a lure slip female connector. The embodiment of FIG. 3 represents the connector 21 being representative of a lure lock male connector. The embodiment of FIG. 5 discloses the connector 23 being representative of an enteral male connector. The embodiment of FIG. 6 discloses the connector 24 being representative of a lure lock female connector. The embodiment of FIG. 7 discloses the connector 25 being representative of a neuraxial male connector. The embodiment of FIG. 8 discloses the connector 26 being representative of a lure slip female connector.

Therefore, it is emphasized that each of a plurality of closures 10 may be manufactured with a predetermined type of connector intended to be compatible with the connector of a medical container, to which it is to be attached. The type or category of connector associated with each of a plurality of different closures 10 are not intended to be limited to the type of connector set forth herein and/or disclosed in the accompanying figures.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure for a medical container comprising:
    a base structured to be operatively supported in an upright orientation and including an exposed face formed on an inner end thereof,
    a connector disposed on said base and structured for attachment to a compatible connector on the medical container,
    said connector mounted on said exposed face and extending outwardly there from,
    a cage including a plurality of cage members each configured to define a helix connected to said base and extending outwardly there from, and
    each of said helices is disposed longitudinally outward from said base and in axially spaced relation to one another and collectively in surrounding relation to said connector.

2. The closure as recited in claim 1 wherein said plurality of cage members defining a helix are structured independently of said connector.

3. The closure as recited in claim 1 wherein said cage includes an open outer end disposed adjacent a free end of said helices; said open outer end structured and dimensioned to define an at least partially restrictive access to said connector.

4. The closure as recited in claim 3 wherein said plurality of cage members are formed of a substantially rigid, at least partially non-collapsible material.

5. The closure assembly as recited in claim 3 wherein said plurality of cage members are formed of a flexible, at least partially collapsible material.

6. The closure as recited in claim 1 wherein said base comprises self-righting structural features including an outer surface having a curved, substantially bulbous configuration extending from an outer periphery of said exposed face to a terminal end segment of said base.

7. The closure as recited in claim 6 wherein said base includes a center of gravity located between a tipping point thereof and said terminal end; said tipping point defined by an outer peripheral edge of said exposed face.

8. The closure as recited in claim 1 further comprising a connector access defined by an open end of at least one of said plurality of cage members disposed axially outward from said connector; said open end of said at least one cage member at least partially defined by free ends of at least one of said plurality of helices.

9. The closure as recited in claim 8 wherein at least some of said plurality of helices are disposed in interruptive relation to the medical container passing into said connector access.

10. The closure as recited in claim 9 wherein said plurality of helices are formed of a substantially rigid non-collapsible material.

11. The closure as recited in claim 9 wherein said plurality of helices are formed of a flexible, at least partially collapsible material.

12. The closure as recited in claim 8 wherein said open end has a larger diameter than said exposed face; at least some of said plurality of helices disposed in interruptive relation to the medical container passing into said open end.

13. A closure for a medical container comprising:
   a base structured to be supported in an operative, upright orientation on a horizontal surface,
   said base including an exposed face and a connector disposed on said exposed face and extending outwardly therefrom,
   a cage including at least one cage member structured independently of said connector and configured in the form of a helix;
   said helix fixedly connected to said exposed face and extending longitudinally and laterally outward from said connector in at least partially surrounding relation thereto, and
   said base comprising a self-righting structure including an outer surface thereof having a curved, substantially bulbous configuration and a center of gravity disposed between a tipping point of said base and a terminal end thereof.

14. The closure as recited in claim 13 wherein said cage comprises a plurality of cage members each configured to define a helix; each of said helices disposed longitudinally outward from said base and in axially spaced relation to one another and collectively in surrounding relation to said connector.

15. The closure as recited in claim 14 further comprising a connector access defined by an open end of said cage disposed axially outward from said connector; said open end of said cage at least partially defined by a collective disposition of free ends of said plurality of helices.

16. The closure as recited in claim 15 wherein said open end has a larger diameter than said exposed face; at least some of said plurality of helices disposed in interruptive relation to the medical container passing into said open end.

17. The closure as recited in claim 13 wherein said plurality of helices are formed of a substantially rigid non-collapsible material.

18. The closure as recited in claim 13 wherein said plurality of helices are formed of a flexible, at least partially collapsible material.

* * * * *